United States Patent
Pellet

(10) Patent No.: US 8,993,561 B2
(45) Date of Patent: Mar. 31, 2015

(54) NITROBENZOTHIAZOLE DERIVATIVES, PREPARATION THEREOF AND THERAPEUTIC APPLICATIONS THEREOF

(75) Inventor: Alain Pellet, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/988,868

(22) PCT Filed: Nov. 18, 2011

(86) PCT No.: PCT/FR2011/052699
§ 371 (c)(1),
(2), (4) Date: May 22, 2013

(87) PCT Pub. No.: WO2012/069743
PCT Pub. Date: May 31, 2012

(65) Prior Publication Data
US 2013/0245008 A1    Sep. 19, 2013

(30) Foreign Application Priority Data
Nov. 22, 2010  (FR) ...................... 10 59602

(51) Int. Cl.
*A61K 31/54* (2006.01)
*C07D 277/62* (2006.01)
*C07D 277/68* (2006.01)
*C07D 417/12* (2006.01)

(52) U.S. Cl.
CPC ............ *C07D 277/68* (2013.01); *C07D 417/12* (2013.01)
USPC ........ 514/228.2; 514/367; 514/338; 514/307; 548/178; 546/146; 546/175

(58) Field of Classification Search
USPC ............... 514/228.2, 367, 338, 307; 548/178; 546/146, 175
See application file for complete search history.

(56) References Cited

U.S. PATENT DOCUMENTS 3,852,298 A * 12/1974 Wagner et al. ................ 548/178

FOREIGN PATENT DOCUMENTS

| DE | 2013434 | 10/1971 |
| DE | 2136923 | 2/1973 |
| DE | 2136924 | 2/1973 |
| JP | 200086642 A | 3/2000 |
| JP | 2000178248 A | 6/2000 |
| WO | WO9965886 A1 | 12/1999 |
| WO | WO0004901 A1 | 2/2000 |
| WO | WO2004067000 A1 | 8/2004 |

OTHER PUBLICATIONS

Amit Nayyar, et al., Recent Advances in New Structural Classes of Anti-Tuberculosis Agents, Current Medicinal Chemistry, (Aug. 1, 2005), vol. 12, No. 16, pp. 1873-1886.
Yoonsang Cho, et al., Discovery of Novel Nitrobenzothiazole Inhibitors for Mycobacterium tuberculosis ATP Phosphoribosyl Transferase (HisG) through Virtual Screening, Journal of Medicinal Chemistry, (Oct. 9, 2008), vol. 51, No. 19, pp. 5984-5992.
International Search Report, dated Jan. 24, 2012 issued in PCT/FR2011/052699. (Previously submitted on May 22, 2013).

* cited by examiner

*Primary Examiner* — Rei-tsang Shiao
(74) *Attorney, Agent, or Firm* — Scully, Scott, Murphy & Presser P.C.

(57) ABSTRACT

The invention relates to the nitrobenzothiazole derivatives of general formula (I): and to the use thereof for treating tuberculosis.

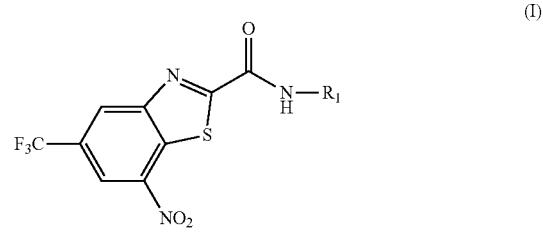

14 Claims, No Drawings

NITROBENZOTHIAZOLE DERIVATIVES, PREPARATION THEREOF AND THERAPEUTIC APPLICATIONS THEREOF

The present invention relates to nitrobenzothiazole derivatives, to the preparation thereof and to the therapeutic use thereof. The compounds according to the present invention are of use in particular in the treatment of tuberculosis.

Tuberculosis is a disease which is still today a threat to world health. Globally, a third of the human population is infected with *Mycobacterium tuberculosis*. Despite the fact that treatments exist and that the disease is curable, tuberculosis killed approximately 1.82 million people in 2008, and its global incidence is increasing by 1% per year, with an estimation in 2008 of 9.4 million new cases of declared disease per year. Added to this are difficulties in terms of correct prescription and of adherence to treatment protocols, and also the emergence of multiresistant *M. tuberculosis* strains. Drug-drug interactions also interfere with the optimal treatment of AIDS and of tuberculosis in coinfected patients.

Common treatment protocols against sensitive *M. tuberculosis* strains are mainly based on a combination of three, or more frequently of four molecules: isoniazid (INH), rifampicin (RIF), pyrazinamide (PZA) and ethambutol (EMB). These drugs constitute the therapeutic "front line".

Over the past few decades, tuberculosis has become resistant to each of these molecules. Strains resistant at least to isoniazid and to rifampicin are denoted "multi-resistant" (MDR-TB). Recently, new strains have appeared which are resistant to a greater number of molecules: those which are resistant to isoniazid, to rifampicin, to fluoroquinolones and to at least one second-line injectable drug are defined as "ultra-resistant"(XDR-TB).

According to an estimation by the WHO carried out in 2009, there were 0.5 million cases of MDR-TB in 2007. Other evaluations report a relative incidence of approximately 11% of multi-resistant strains among all the new cases of tuberculosis.

Another therapeutic drawback in the treatment of tuberculosis is the interaction of rifampicin with treatments against HIV (Human Immunodeficiency Virus), which represents an obstacle in the treatment of patients coinfected with tuberculosis and HIV. The current therapeutic recommendations against HIV favor, as front-line treatment, an antiretroviral tritherapy combining a protease inhibitor (PI) or a non-nucleoside reverse transcriptase inhibitor (NNRTI) with two nucleoside reverse transcriptase inhibitors (NRTIs). PI and NNRTI are metabolized by CYP3A4. Metabolic interactions between antiretrovirals (ARVs) and certain combined drugs have been demonstrated. Thus, rifampicin, which is a powerful inducer of intestinal and hepatic CYP3A4, reduces ARV concentrations.

There is an urgent need to develop improved therapies against tuberculosis. These new treatments against tuberculosis should preferably meet one or more of the following criteria:
- shorten the treatment duration in order to improve adherence to treatment protocols and to reduce the appearance of resistant bacteria,
- be well tolerated, acting via new mechanisms of action and therefore effective against multi-resistant and/or ultra-resistant strains,
- be active against tuberculosis and exhibit neither inhibition nor induction of the hepatic cytochrome P450 enzyme, so as to avoid drug interactions, in particular with antiretroviral therapies, in order to facilitate the treatment of patients coinfected with tuberculosis and HIV,
- have a shortened treatment time for latent tuberculosis (asymptomatic primary infection) so as to address the problem of the biological reservoir of *M. tuberculosis*.

The subject of the present invention is in particular nitrobenzothiazole derivatives which have a bacteriostatic and also bactericidal action against *Mycobacterium* or *Corynebacterium* strains sensitive and resistant to front-line antibiotics, the preparation thereof and the therapeutic uses thereof.

Benzothiazoles have been described in compositions used as insect, mite and tick repellents (WO 99/65886) and as cell adhesion inhibitors (JP2000086642).

Benzothiazoles have also been described in the preparation of immunostimulant compounds for treating infectious diseases, tumors and immune diseases (JP2000178248).

Nitrobenzothiazoles have been described as fungicides and bactericides (DE 2136924 and DE 2136923).

A subject of the present invention is the compounds corresponding to formula (I):

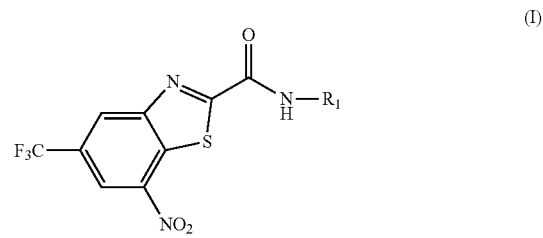

for which, $R_1$ represents:
  a $(C_1-C_4)$alkyl substituted with:
    one or more halogen atoms;
    an aryl optionally substituted with one or more groups chosen, independently of one another, from an OH, $(C_1-C_3)$alkoxy, $(C_3-C_6)$ heterocycloalkyl or $(C_1-C_3)$ fluoroalkoxy group and a halogen atom;
    a heteroaryl optionally substituted with one or more groups chosen, independently of one another, from a $(C_1-C_4)$alkyl group and a halogen atom;
    an unsubstituted heteroaryl-NH;
    an unsubstituted $(C_3-C_6)$cycloalkyl;
    a $(C_3-C_6)$heterocycloalkyl optionally substituted with one or more groups chosen, independently of one another, from a $(C_1-C_3)$ alkyl, aryl and aryl $(C_1-C_3)$ alkyl group;
or
  a $(C_1-C_4)$alkyl disubstituted with:
    an unsubstituted aryl;
    and
    an unsubstituted $(C_3-C_6)$heterocycloalkyl.

The compounds of general formula (I) can comprise one or more asymmetric carbons. They can therefore exist in the form of enantiomers or of diastereoisomers. These enantiomers and diastereoisomers, and also mixtures thereof, including racemic mixtures, form part of the invention.

By virtue of their structure, the compounds of general formula (I) can also exist in the form of isomers of rotamer or atropoisomer type.

The compounds of formula (I) can also exist in the form of bases or of addition salts with acids or with bases. Such addition salts form part of the invention.

These salts are advantageously prepared with pharmaceutically acceptable acids or bases, but the salts of other acids or bases that are of use, for example, for purifying or separating the compounds of general formula (I) also form part of the invention.

According to the present invention, the N-oxides of the compounds comprising a nitrogen atom of tertiary type or nitrogenous heteroaryl compounds also form part of the invention, with the exception of compounds of benzothiazole-N-oxide type.

The compounds of formula (I) according to the present invention also comprise those in which one or more hydrogen, carbon or halogen, in particular chlorine or fluorine, atoms have been replaced with their radioactive isotopes, for example tritium for replacing hydrogen or carbon 14 for replacing carbon 12. Such labeled compounds are of use in research, metabolism or pharmacokinetic studies, and also in biological and pharmacological tests as tools.

In the context of the present invention:

- in $C_m$-$C_n$, the numerical indices m and n determine the possible number of carbon atoms present in a chain or in a ring. Thus, by way of example, $C_1$-$C_6$ represents a linear or branched carbon-based chain which can have from 1 to 6 carbon atoms, or alternatively $C_0$-$C_6$ represents a linear or branched carbon-based chain which can have from 0 to 6 carbon atoms;
- alkyl represents a linear or branched, saturated aliphatic group; for example, a ($C_1$-$C_6$)alkyl group represents a linear or branched carbon-based chain having from 1 to 6 carbon atoms, in particular a methyl, ethyl, propyl, isopropyl, butyl, isobutyl, sec-butyl, tert-butyl, pentyl; when an alkyl group is substituted with one or more halogen atoms or with one or more groups as indicated in the definitions, these substitutions can be borne by the same carbon atom and/or by different carbon atoms;
- cycloalkyl represents a saturated cyclic aliphatic group. By way of example, mention may be made of cyclopropyl, cyclobutyl, cyclopentyl and cyclohexyl groups;
- halogen represents a fluorine, chlorine, bromine or iodine atom;
- fluoroalkyl represents an alkyl group in which one or more hydrogen atoms are replaced with a fluorine atom. By way of example of a fluoroalkyl group, mention may be made of trifluoromethyl, difluoromethyl and 3,3,3-trifluoropropyl;
- heterocycloalkyl represents an optionally substituted, monocyclic or polycyclic, saturated or partially saturated ring comprising from 3 to 6 ring members and one or more heteroatoms such as nitrogen, oxygen or sulfur atoms. By way of example, a heterocycloalkyl can be a pyrrolidine, a morpholine, a piperazine, a diazetidine, a dihydropyrrolidine, a piperidine, an azepane, an imidazolidine, a thiomorpholine, a tetrahydropyran, a tetrahydrothiopyran, a piperazine, a diazepane or an azabicyclooctane, a tropane or a 3,6-diazabicyclo[3.1.0]hexane;
- aryl represents an optionally substituted monocyclic or polycyclic aromatic system comprising from 6 to 14 carbon atoms, preferably from 6 to 10 carbon atoms. When the system is polycyclic, at least one of the rings is aromatic. By way of examples of aryl groups, mention may be made of phenyl, naphthyl, indanyl, tetrahydronaphthyl, anthracenyl or azulenyl;
- heteroaryl represents an optionally substituted monocyclic or polycyclic aromatic system comprising from 5 to 14 ring members, preferably from 5 to 10 ring members and comprising one or more heteroatoms such as nitrogen, oxygen or sulfur atoms. When the system is polycyclic, at least one of the rings is aromatic. The nitrogen atoms may be in the form of N-oxides. By way of example of monocyclic heteroaryls, mention may be made of thiazole, thiadiazole, thiophene, imidazole, triazole, tetrazole, pyridine, furan, oxazole, isoxazole, oxadiazole, pyrrole, pyrazole, pyrimidine, pyridazine and pyrazine. By way of example of polycyclic heteroaryls, mention may be made of indole, benzofuran, benzimidazole, benzothiophene, benzotriazole, benzothiazole, benzoxazole, quinoline, isoquinoline, indazole, quinazoline, phthalazine, quinoxaline, naphthyridine, 2,3-dihydro-1H-indole, 2,3-dihydrobenzofuran, tetrahydroquinoline, tetrahydroisoquinoline or tetrahydroisoquinazoline;
- alkoxy represents an —O($C_m$-$C_n$)alkyl group comprising a linear or branched, saturated aliphatic chain. By way of example of alkoxy groups, mention may be made of methoxy;
- fluoroalkoxy represents an alkoxy group in which one or more hydrogen atoms are replaced with a fluorine atom. By way of examples of a fluoroalkoxy group, mention may be made of the groups —O—$CHF_2$, —O—$CF_3$ or —O—$CF_2$—$CF_3$;
- aryloxy represents an —O-aryl group;
- heteroaryloxy represents an —O-heteroaryl group;
- hydroxyalkyl represents a —($C_1$-$C_6$)alkyl-OH group. By way of example of a hydroxyalkyl group, mention may be made of the group —$CH_2$—OH.

According to the present invention, preference is given to the compounds of formula (I) wherein $R_1$ represents:

a ($C_1$-$C_4$)alkyl radical substituted with:

- one or more fluorine atoms;
- a phenyl optionally substituted with one or more groups chosen, independently of one another, from an OH, methoxy, morpholine or trifluoromethoxy group and a chlorine or fluorine atom;
- a pyridinyl, isoxazolyl, pyrazolyl, thienyl, benzoxazolyl, tetrahydroisoquinolinyl, quinolinyl and thiazolyl group optionally substituted with one or more groups chosen, independently of one another, from a methyl or ethyl group or a chlorine atom;
- an unsubstituted pyridinyl-NH group;
- an unsubstituted cyclohexyl group;
- a tetrahydropyranyl group, a morpholinyl group, a pyrrolidinyl group and a thiomorpholinyl group optionally substituted with one or more groups chosen, independently of one another, from a methyl, phenyl and benzyl group;

or a ($C_1$-$C_4$)alkyl radical disubstituted with:

- an unsubstituted phenyl;

and

- an unsubstituted morpholinyl group.

Among the compounds according to the invention, mention may in particular be made of the compounds hereinafter, as they are, and also the salts thereof:

| Chemical structure | IUPAC name |
|---|---|
| 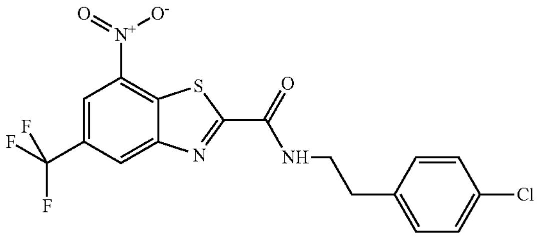 [SMILES: O=C(NCCc1ccc(Cl)cc1)c1nc2cc(C(F)(F)F)cc([N+](=O)[O-])c2s1] | N-[2-(4-chlorophenyl)ethyl]-7-nitro-5-(trifluoromethyl)-1,3-benzothiazole-2-carboxamide |
| 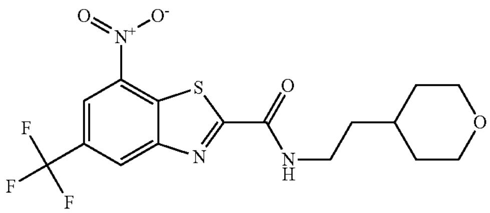 [SMILES: O=C(NCCC1CCOCC1)c1nc2cc(C(F)(F)F)cc([N+](=O)[O-])c2s1] | 7-nitro-N-[2-(tetrahydro-2H-pyran-4-yl)ethyl]-5-(trifluoromethyl)-1,3-benzothiazole-2-carboxamide |
| 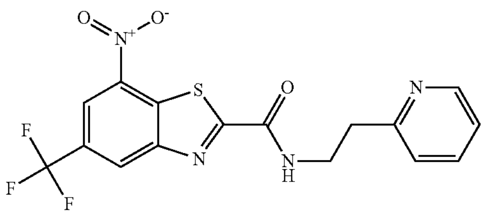 [SMILES: O=C(NCCc1ccccn1)c1nc2cc(C(F)(F)F)cc([N+](=O)[O-])c2s1] | 7-nitro-N-(2-pyridin-2-ylethyl)-5-(trifluoromethyl)-1,3-benzothiazole-2-carboxamide |
| 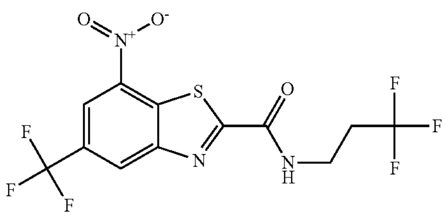 [SMILES: O=C(NCCC(F)(F)F)c1nc2cc(C(F)(F)F)cc([N+](=O)[O-])c2s1] | 7-nitro-5-(trifluoromethyl)-N-(3,3,3-trifluoropropyl)-2-benzothiazolecarboxamide |
| 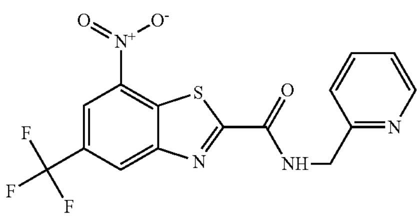 [SMILES: O=C(NCc1ccccn1)c1nc2cc(C(F)(F)F)cc([N+](=O)[O-])c2s1] | 7-nitro-N-(pyridine-2-ylmethyl)-5-(trifluoromethyl)-1,3-benzothiazole-2-carboxamide |
| 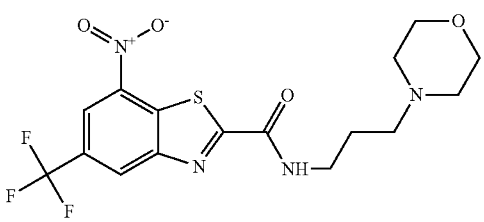 [SMILES: O=C(NCCCN1CCOCC1)c1nc2cc(C(F)(F)F)cc([N+](=O)[O-])c2s1] | N-[3-(4-morpholinyl)propyl]-7-nitro-5-(trifluoromethyl)-2-benzothiazolecarboxamide |
| 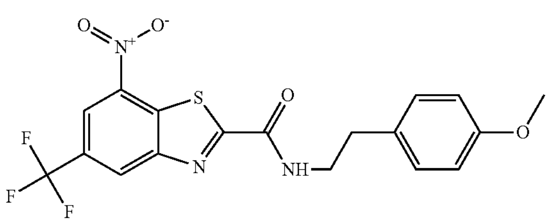 [SMILES: COc1ccc(CCNC(=O)c2nc3cc(C(F)(F)F)cc([N+](=O)[O-])c3s2)cc1] | N-[2-(4-methoxyphenyl)ethyl]-7-nitro-5-(trifluoromethyl)-1,3-benzothiazole-2-carboxamide |

| Chemical structure | IUPAC name |
|---|---|
| 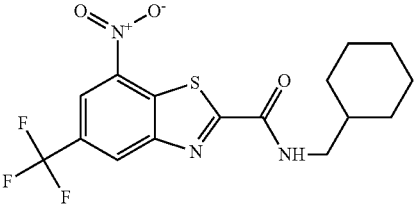 [SMILES: O=C(NCC1CCCCC1)c1nc2cc(C(F)(F)F)cc([N+](=O)[O-])c2s1] | N-(cyclohexylmethyl)-7-nitro-5-(trifluoromethyl)-1,3-benzothiazole-2-carboxamide |
| 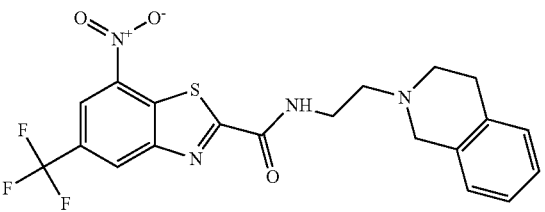 [SMILES: O=C(NCCN1CCc2ccccc2C1)c1nc2cc(C(F)(F)F)cc([N+](=O)[O-])c2s1] | N-[2-(1,2,3,4-tetrahydroisoquinolin-2(1H)-yl)ethyl]-7-nitro-5-(trifluoromethyl)-1,3-benzothiazole-2-carboxamide |
| 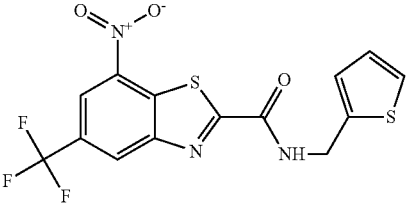 [SMILES: O=C(NCc1cccs1)c1nc2cc(C(F)(F)F)cc([N+](=O)[O-])c2s1] | 7-nitro-N-(thien-2-ylmethyl)-5-(trifluoromethyl)-1,3-benzothiazole-2-carboxamide |
| 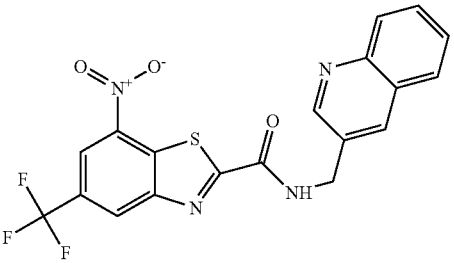 [SMILES: O=C(NCc1cnc2ccccc2c1)c1nc2cc(C(F)(F)F)cc([N+](=O)[O-])c2s1] | 7-nitro-N-(quinolin-3-ylmethyl)-5-(trifluoromethyl)-1,3-benzothiazole-2-carboxamide |
| 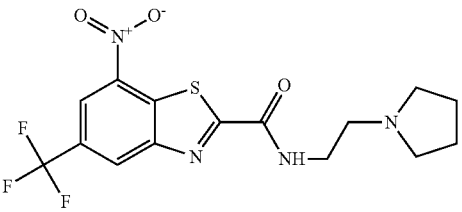 [SMILES: O=C(NCCN1CCCC1)c1nc2cc(C(F)(F)F)cc([N+](=O)[O-])c2s1] | 7-nitro-N-(2-pyrrolidin-1-ylethyl)-5-(trifluoromethyl)-1,3-benzothiazole-2-carboxamide |
| 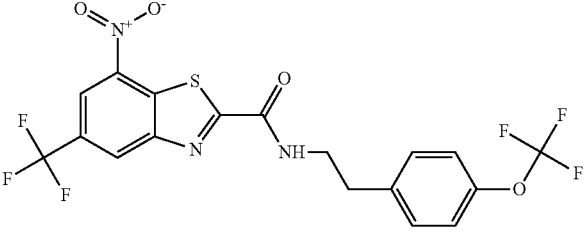 [SMILES: O=C(NCCc1ccc(OC(F)(F)F)cc1)c1nc2cc(C(F)(F)F)cc([N+](=O)[O-])c2s1] | 7-nitro-N-{2-[4-trifluoromethoxy)phenyl]-ethyl}-5-(trifluoromethyl)-1,3-benzothiazole-2-carboxamide |

| Chemical structure | IUPAC name |
| --- | --- |
| 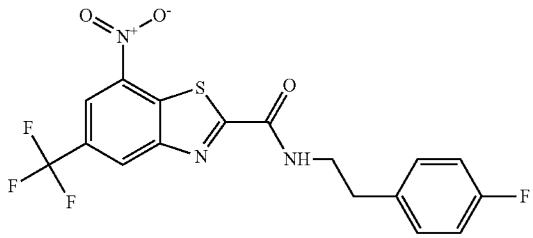 [SMILES: O=C(NCCc1ccc(F)cc1)c1nc2cc(C(F)(F)F)cc([N+](=O)[O-])c2s1] | N-[2-(4-fluorophenyl)ethyl]-7-nitro-5-(trifluoromethyl)-1,3-benzothiazole-2-carboxamide |
| 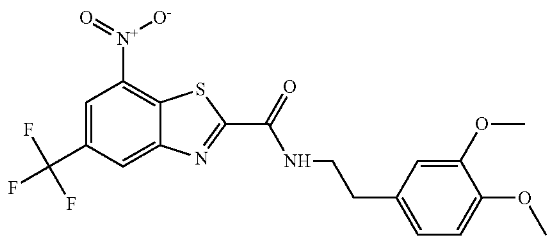 [SMILES: COc1ccc(CCNC(=O)c2nc3cc(C(F)(F)F)cc([N+](=O)[O-])c3s2)cc1OC] | N-[2-(3,4-dimethoxyphenyl)ethyl]-7-nitro-5-(trifluoromethyl)-1,3-benzothiazole-2-carboxamide |
| 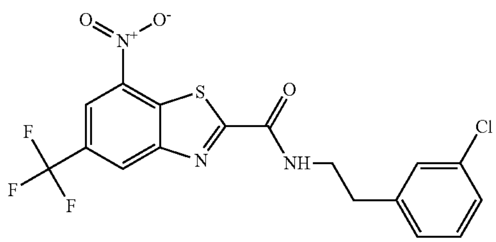 [SMILES: O=C(NCCc1cccc(Cl)c1)c1nc2cc(C(F)(F)F)cc([N+](=O)[O-])c2s1] | N-[2-(3-a chlorophenyl)ethyl]-7-nitro-5-(trifluoromethyl)-1,3-benzothiazole-2-carboxamide |
| 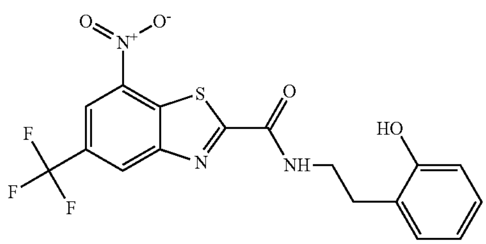 [SMILES: O=C(NCCc1ccccc1O)c1nc2cc(C(F)(F)F)cc([N+](=O)[O-])c2s1] | N-[2-(2-hydroxyphenyl)ethyl]-7-nitro-5-(trifluoromethyl)-1,3-benzothiazole-2-carboxamide |
| 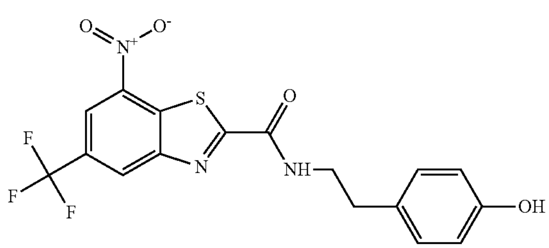 [SMILES: O=C(NCCc1ccc(O)cc1)c1nc2cc(C(F)(F)F)cc([N+](=O)[O-])c2s1] | N-[2-(4-hydroxyphenyl)ethyl]-7-nitro-5-(trifluoromethyl)-1,3-benzothiazole-2-carboxamide |
| 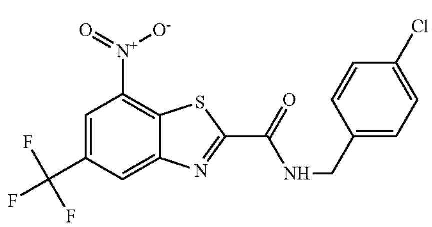 [SMILES: O=C(NCc1ccc(Cl)cc1)c1nc2cc(C(F)(F)F)cc([N+](=O)[O-])c2s1] | N-(4-chlorobenzyl)-7-nitro-5-(trifluoromethyl)-1,3-benzothiazole-2-carboxamide |

| Chemical structure | IUPAC name |
|---|---|
| 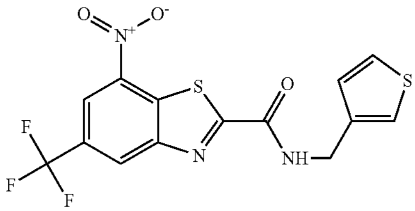 [SMILES: O=C(NCc1ccsc1)c1nc2cc(C(F)(F)F)cc([N+](=O)[O-])c2s1] | 7-nitro-N-(thien-3-ylmethyl)-5-(trifluoromethyl)-1,3-benzothiazole-2-carboxamide |
| 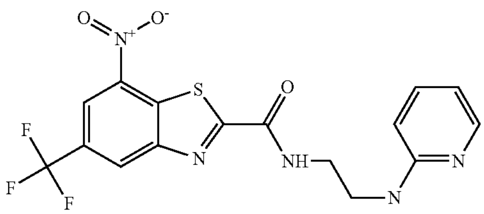 [SMILES: O=C(NCCNc1ccccn1)c1nc2cc(C(F)(F)F)cc([N+](=O)[O-])c2s1] | 7-nitro-N-[2-(pyridin-2-ylamino)ethyl]-5-(trifluoromethyl)-1,3-benzothiazole-2-carboxamide |
| 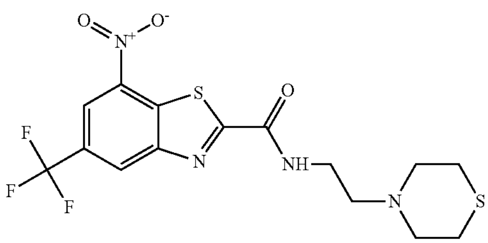 | 7-nitro-N-[2-thiomorpholin-4-ylethyl)-5-(trifluoromethyl)-1,3-benzothiazole-2-carboxamide |
| 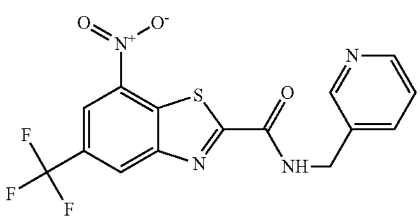 [SMILES: O=C(NCc1cccnc1)c1nc2cc(C(F)(F)F)cc([N+](=O)[O-])c2s1] | 7-nitro-N-(pyridin-3-ylmethyl)-5-(trifluoromethyl)-1,3-benzothiazole-2-carboxamide |
| 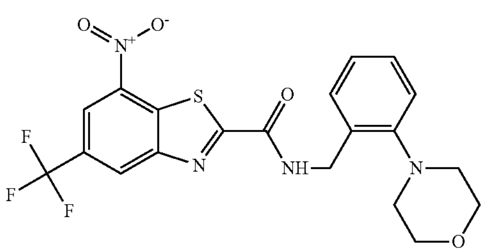 [SMILES: O=C(NCc1ccccc1N1CCOCC1)c1nc2cc(C(F)(F)F)cc([N+](=O)[O-])c2s1] | N-(2-morpholin-4-ylbenzyl)-7-nitro-5-(trifluoromethyl)-1,3-benzothiazole-2-carboxamide |
| 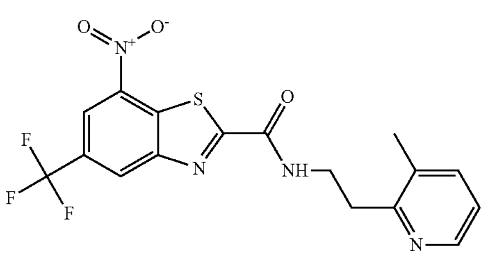 [SMILES: Cc1cccnc1CCNC(=O)c1nc2cc(C(F)(F)F)cc([N+](=O)[O-])c2s1] | N-[2-(3-methylpyridin-2-yl)ethyl]-7-nitro-5-(trifluoromethyl)-1,3-benzothiazole-2-carboxamide |

| Chemical structure | IUPAC name |
|---|---|
| 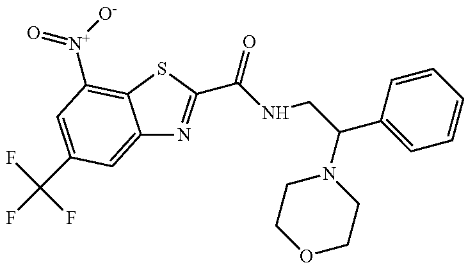 [SMILES: O=C(NCC(c1ccccc1)N1CCOCC1)c1nc2cc(C(F)(F)F)cc([N+](=O)[O-])c2s1] | N-(2-morpholin-4-yl-2-phenylethyl)-7-nitro-5-(trifluoromethyl)-1,3-benzothiazole-2-carboxamide |
| 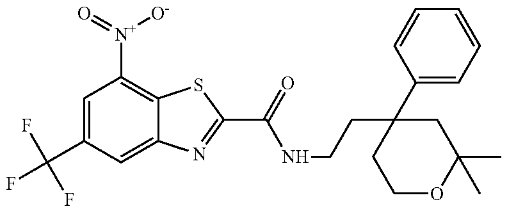 [SMILES: CC1(C)CC(CCNC(=O)c2nc3cc(C(F)(F)F)cc([N+](=O)[O-])c3s2)(c2ccccc2)CCO1] | N-[2-(2,2-dimethyl-4-phenyltetrahydro-2H-pyran-4-yl)ethyl]-7-nitro-5-(trifluoromethyl)-1,3-benzothiazole-2-carboxamide |
| 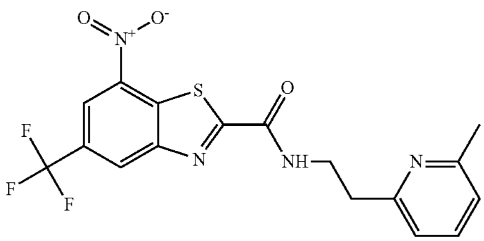 [SMILES: Cc1cccc(CCNC(=O)c2nc3cc(C(F)(F)F)cc([N+](=O)[O-])c3s2)n1] | N-[2-(6-methylpyridin-2-yl)ethyl]-7-nitro-5-(trifluoromethyl)-1,3-benzothiazole-2-carboxamide |
| 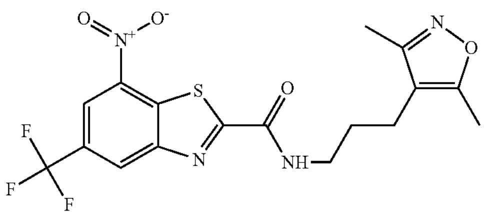 [SMILES: Cc1noc(C)c1CCCNC(=O)c1nc2cc(C(F)(F)F)cc([N+](=O)[O-])c2s1] | N-[3-(3,5-dimethylisoxazol-4-yl)propyl]-7-nitro-5-(trifluoromethyl)-1,3-benzothiazole-2-carboxamide |
| 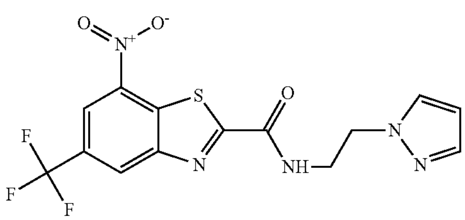 [SMILES: O=C(NCCn1cccn1)c1nc2cc(C(F)(F)F)cc([N+](=O)[O-])c2s1] | 7-nitro-N-[2-(1H-pyrazol-1-yl)ethyl]-5-(trifluoromethyl)-1,3-benzothiazole-2-carboxamide |
| 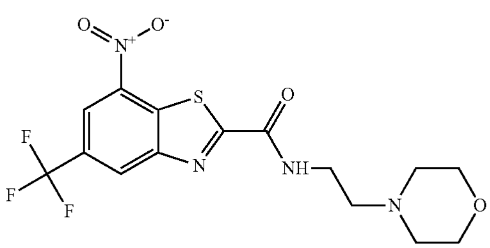 [SMILES: O=C(NCCN1CCOCC1)c1nc2cc(C(F)(F)F)cc([N+](=O)[O-])c2s1] | N-(2-morpholin-4-ylethyl)-7-nitro-5-(trifluoromethyl)-1,3-benzothiazole-2-carboxamide |

-continued

| Chemical structure | IUPAC name |
|---|---|
| 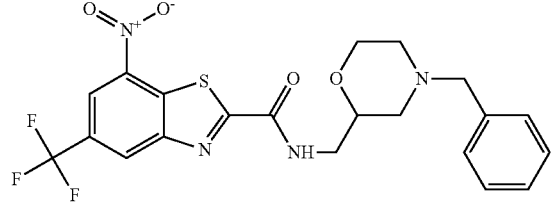 [SMILES: O=C(NCC1CN(Cc2ccccc2)CCO1)c1nc2cc(C(F)(F)F)cc([N+](=O)[O-])c2s1] | N-[(4-benzylmorpholin-2-yl)methyl]-7-nitro-5-(trifluoromethyl)-1,3-benzothiazole-2-carboxamide |
| 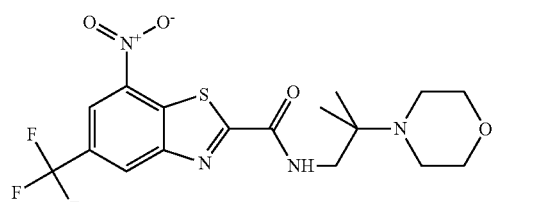 | N-(2-methyl-2-morpholin-4-ylpropyl)-7-nitro-5-(trifluoromethyl)-1,3-benzothiazole-2-carboxamide |
| 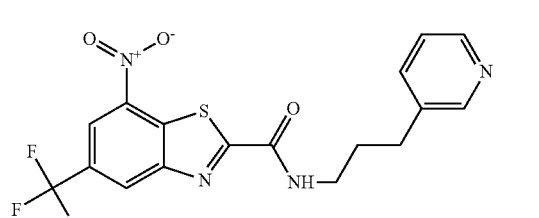 | 7-nitro-N-(3-pyridin-3-ylpropyl)-5-(trifluoromethyl)-1,3-benzothiazole-2-carboxamide |
| 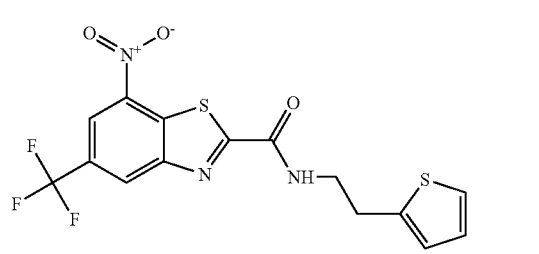 [SMILES: O=C(NCCc1cccs1)c1nc2cc(C(F)(F)F)cc([N+](=O)[O-])c2s1] | 7-nitro-N-(2-thien-2-ylethyl)-5-(trifluoromethyl)-1,3-benzothiazole-2-carboxamide |
| 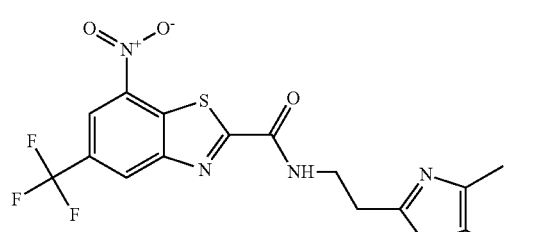 | N-[2-(5-chloro-4-methyl-1,3-thiazol-2-yl)ethyl]-7-nitro-5-(trifluoromethyl)-1,3-benzothiazole-2-carboxamide |
| 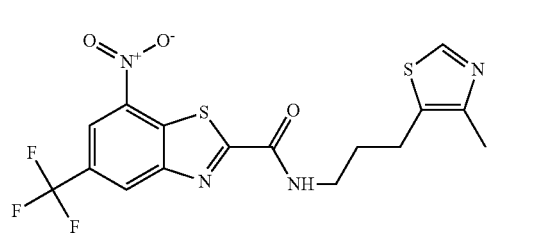 [SMILES: Cc1ncsc1CCCNC(=O)c1nc2cc(C(F)(F)F)cc([N+](=O)[O-])c2s1] | N-[3-(4-methyl-1,3-thiazol-5-yl)propyl]-7-nitro-5-(trifluoromethyl)-1,3-benzothiazole-2-carboxamide |

| Chemical structure | IUPAC name |
|---|---|
| 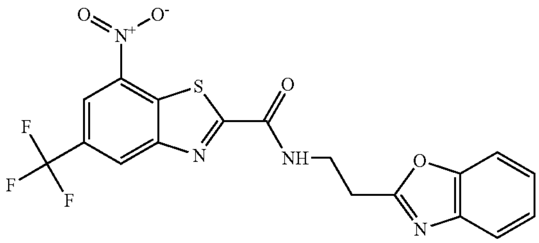 [SMILES: O=C(NCCc1nc2ccccc2o1)c1nc2cc(C(F)(F)F)cc([N+](=O)[O-])c2s1] | N-[2-(1,3-benzoxazol-2-yl)ethyl]-7-nitro-5-(trifluoromethyl)-1,3-benzothiazole-2-carboxamide |
| 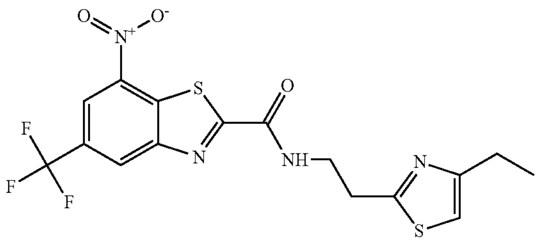 [SMILES: CCc1csc(CCNC(=O)c2nc3cc(C(F)(F)F)cc([N+](=O)[O-])c3s2)n1] | N-[2-(4-ethyl-1,3-thiazol-2-yl)ethyl]-7-nitro-5-(trifluoromethyl)-1,3-benzothiazole-2-carboxamide |
| 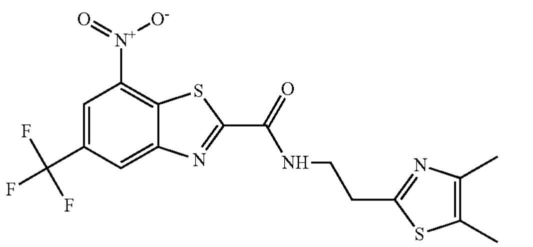 [SMILES: Cc1nc(CCNC(=O)c2nc3cc(C(F)(F)F)cc([N+](=O)[O-])c3s2)sc1C] | N-[2-(4,5-dimethyl-1,3-thiazol-2-yl)ethyl]-7-nitro-5-(trifluoromethyl)-1,3-benzothiazole-2-carboxamide |

Preference is most particularly given to the following compounds and salts thereof:

- N-[2-(4-chlorophenyl)ethyl]-7-nitro-5-(trifluoromethyl)-1,3-benzothiazole-2-carboxamide;
- 7-nitro-N-[2-(tetrahydro-2H-pyran-4-yl)ethyl]-5-(trifluoromethyl)-1,3-benzothiazole-2-carboxamide;
- N-[2-(4-methoxyphenyl)ethyl]-7-nitro-5-(trifluoromethyl)-1,3-benzothiazole-2-carboxamide;
- N-[2-(1,2,3,4-tetrahydroisoquinolin-2(1H)-yl)ethyl]-7-nitro-5-(trifluoromethyl)-1,3-benzothiazole-2-carboxamide;
- N-[2-(4-fluorophenyl)ethyl]-7-nitro-5-(trifluoromethyl)-1,3-benzothiazole-2-carboxamide;
- N-[2-(3,4-dimethoxyphenyl)ethyl]-7-nitro-5-(trifluoromethyl)-1,3-benzothiazole-2-carboxamide;
- N-[2-(3-chlorophenyl)ethyl]-7-nitro-5-(trifluoromethyl)-1,3-benzothiazole-2-carboxamide;
- N-[2-(2-hydroxyphenyl)ethyl]-7-nitro-5-(trifluoromethyl)-1,3-benzothiazole-2-carboxamide;
- N-[2-(4-hydroxyphenyl)ethyl]-7-nitro-5-(trifluoromethyl)-1,3-benzothiazole-2-carboxamide;
- 7-nitro-N-[2-(pyridin-2-ylamino)ethyl]-5-(trifluoromethyl)-1,3-benzothiazole-2-carboxamide;
- 7-nitro-N-[2-thiomorpholin-4-ylethyl]-5-(trifluoromethyl)-1,3-benzothiazole-2-carboxamide;
- N-[2-(3-methylpyridin-2-yl)ethyl]-7-nitro-5-(trifluoromethyl)-1,3-benzothiazole-2-carboxamide;
- N-(2-morpholin-4-yl-2-phenylethyl)-7-nitro-5-(trifluoromethyl)-1,3-benzothiazole-2-carboxamide;
- N-[2-(2,2-dimethyl-4-phenyltetrahydro-2H-pyran-4-yl)ethyl]-7-nitro-5-(trifluoromethyl)-1,3-benzothiazole-2-carboxamide;
- N-[2-(5-chloro-4-methyl-1,3-thiazol-2-yl)ethyl]-7-nitro-5-(trifluoromethyl)-1,3-benzothiazole-2-carboxamide;
- N-[2-(1,3-benzoxazol-2-yl)ethyl]-7-nitro-5-(trifluoromethyl)-1,3-benzothiazole-2-carboxamide;
- N-[2-(4-ethyl-1,3-thiazol-2-yl)ethyl]-7-nitro-5-(trifluoromethyl)-1,3-benzothiazole-2-carboxamide;
- N-[2-(4,5-dimethyl-1,3-thiazol-2-yl)ethyl]-7-nitro-5-(trifluoromethyl)-1,3-benzothiazole-2-carboxamide.

In the text that follows, the term "protective group PG" is intended to mean a group which makes it possible, on the one hand, to protect a reactive function such as a hydroxyl or an amine during a synthesis and, on the other hand, to regenerate the intact reactive function at the end of synthesis. Examples of protective groups and also methods of protection and deprotection are given in "Protective Group in Organic Synthesis", Green et al., 4th Edition, John Wiley & Sons, Inc., New York, 2007.

In the text which follows, the term "LG" is intended to mean a group that can be easily cleaved from a molecule by breaking a heterolytic bond, with the departure of a pair of electrons. This group can thus be easily replaced with another group in a substitution reaction, for example. Such leaving groups are, for example, halogens or an activated hydroxyl group such as a methanesulfonate, benzenesulfonate, p-toluenesulfonate, triflate, acetate, etc. Examples of leaving groups and also references for the preparation thereof are given in "Advanced Organic Chemistry", M. B. Smith and J. March, 6th Edition, Wiley Interscience, 2007, p. 496-501.

In accordance with the invention, the compounds of general formula (I) can be prepared according to the process (route A) characterized in that a compound of formula (II):

(II)

[Structure: benzothiazole with F₃C- substituent, NO₂, and C(=O)OR group]

wherein R represents a ($C_1$-$C_4$)alkyl, is reacted with an amine of formula (III):

$$H_2N-R_1 \quad (III)$$

wherein $R_1$ is as defined for the compounds of formula (I).

The reaction is optionally carried out in the presence of an inorganic or organic base in the case where the secondary amine of formula (III) is in the form of an acid salt (for example hydrochloride) in a polar solvent such as an alcohol, DMF or DMSO, and at a temperature of between 5° C. and 100° C.

The reaction is preferably carried out in MeOH at AT, optionally with triethylamine.

According to one variant (route B), the compounds of formula (I) can be prepared according to the process characterized in that a reaction is carried out comprising the reduction of the compounds of formula (IV) having a benzothiazole N-oxide nucleus:

(IV)

[Structure: benzothiazole N-oxide with F₃C-, NO₂, and C(=O)NH-R₁ group]

wherein $R_1$ is as defined for the compounds of formula (I).

The reaction is preferably carried out using a trivalent phosphorus-containing reagent such as triethyl phosphite, in an alcohol such as ethanol (Wagner et al., *Chem. Ber.* 1973, 106, 640-654).

The compounds of formula (II) wherein R represents a ($C_1$-$C_4$)alkyl are obtained by reduction of the corresponding N-oxide derivatives of formula (V):

(V)

[Structure: benzothiazole N-oxide with F₃C-, NO₂, and C(=O)O-R group]

wherein R represents a ($C_1$-$C_4$)alkyl.

The reaction is carried out using a trivalent phosphorus-containing reagent such as triethyl phosphite, in an alcohol such as ethanol (Wagner et al. *Chem. Ber.* 1973, 106, 640-654).

The compounds of formula (III) are commercially available or described in the literature, or else can be prepared according to methods which are described therein or which are known to those skilled in the art.

The compounds of formula (IV) which have a benzothiazole N-oxide nucleus, wherein $R_1$ is as defined for the compounds of formula (I), are obtained by reacting the corresponding N-oxide derivatives of formula (V), wherein R represents a ($C_1$-$C_4$)alkyl, with an amine of formula (III) wherein $R_1$ is as defined for the compounds of formula (I).

The reaction is carried out at between 5 and 100° C., in a polar solvent such as an alcohol, DMF or DMSO, optionally in the presence of an inorganic or organic base in the case where the secondary amine of formula (III) is in the form of an acid salt (for example hydrochloride). The reaction is preferably carried out in MeOH at AT, optionally in the presence of triethylamine.

The compounds of formula (V) wherein R represents a ($C_1$-$C_4$)alkyl are known or described (for example, in Wagner et al, Chem. Ber. 1973, 106, 640-654) or else prepared by reacting a thioglycolic acid ester of formula (VI):

(VI)

$$HS\frown CO_2R$$

wherein R represents a ($C_1$-$C_4$)alkyl, with a compound of formula (VII):

(VII)

[Structure: benzene ring with F₃C-, NO₂ (×2), and LG substituents]

in which LG represents a leaving group, preferably a halogen.

The compounds of formulae (VI) and (VII) are commercially available or prepared according to the methods described in the literature.

The following examples describe the preparation of some compounds in accordance with the invention. These examples are not limiting and merely illustrate the present invention. The numbers of the compounds exemplified refer back to those given in table I hereinafter, which illustrates the chemical structures and the physical properties of some compounds according to the invention.

The melting points (MP) are expressed in degrees Celsius. They were measured either with a Köffler instrument (cited as (K) in the subsequent text), or with a Mettler-Toledo FP62 instrument (cited as (M) in the subsequent text).

The commercially available chemical reagents and also the reaction or chromatography solvents are used without prior purification or distillation.

The reactions are monitored by thin layer chromatography (60F254 silica gel, Merck) with UV detection at 254 nm or detection by spraying a solution of 2/3/10/10 Draggendorff reagent/AcOH/$H_2O$/EtOH or by spraying a solution of 0.5% ninhydrin/n-butanol (Prolabo), followed by heating at –100° C.

Generally, the solvents are eliminated in a rotary evaporator under reduced pressure at 40° C.

The chromatography purifications are carried out on an Isco Combiflash system using Redisep or Chromabond Flash RS 6 SiOH preconditioned silica cartridges or by automated HPLC (Waters 2767 autosampler, Waters 2525 pump, Waters ZQ MS detector) on a Waters sunfire C18 column (30×100 mm), PDA: Waters 2926.

The LCMS analyses are carried out:
on a Waters 1525 HPLC system (MUX 2488 UV detector, 220 nm) coupled to a Waters LCT mass spectrometer, ionization by MUX 8, ESI⁺ positive mode (method A) or ESI⁻ negative mode (method B);
on an Agilent series 1100 HPLC system (UV detection at 220 nm) coupled to an MSD SL mass spectrometer (Agilent), ionization by positive mode electrospray ESI⁺, software: Chemstation version B.01.03 from Agilent (method C).

| Method | A | B | C |
|---|---|---|---|
| column | Waters UPLC BEH C18 50 × 2.1 mm; 1.7 μm 55° C. | Waters UPLC BEH C18 50 × 2.1 mm; 1.7 μm 55° C. | C18 Symetry 50 × 2.1 mm; 3.54 μm |
| solvents | MeCN + 0.08% TFA: $H_2O$ + 0.1% TFA | MeCN + 0.08% TFA: $H_2O$ + 0.1% TFA | MeCN + 0.005% TFA: $H_2O$ + 0.005% TFA |
| gradient | 5:95 to 95:5 (1.1 min) to 95:5 (1.7 min) | 5:95 to 95:5 (1.1 min) to 95:5 (1.7 min) | 0:100 to 100:0 (10 min) to 100:0 (5 min) |
| flow rate | 0.9 ml/min | 0.9 ml/min | 0.4 ml/min |
| ionization | ESI⁺ | ESI⁻ | ESI⁺ |

The LCMS analytical characteristics of the products are the m/z ratio of the ion $(M^+H)^+$ or of the ion $(M^-H)^-$ and the retention time (tr) of the corresponding peak, observed under UV, most commonly at 220 nm, and expressed in minutes.

The proton nuclear magnetic resonance (¹H NMR) spectra were performed at 300 MHz, 400 MHz or 500 MHz on Brüker instruments. The abbreviations used to characterize the signals are the following: s=singlet, m=multiplet, d=doublet, t=triplet, q=quadruplet.

The abbreviations and symbols used for the description of the synthesis procedures and for the description of the compounds are the following:
DMF for dimethylformamide,
DMSO for dimethyl sulfoxide,
THF for tetrahydrofuran,
HCl for hydrochloric acid,
HBr for hydrobromic acid,
NaOH for sodium hydroxide,
Et for ethyl,
Me for methyl,
TFA for trifluoroacetic acid,
AT for ambient temperature,
NMP for N-methylpyrrolidinone,
APS for automated parallel synthesis,
BOC for tert-butyloxycarbonyl,
LCMS for liquid chromatography coupled with mass spectrometry.

PREPARATION OF COMPOUND NO. 1

Example 1—Route B

N-[2-(4-chlorophenyl)ethyl]-7-nitro-5-(trifluoromethyl)-1,3-benzothiazole-2-carboxamide

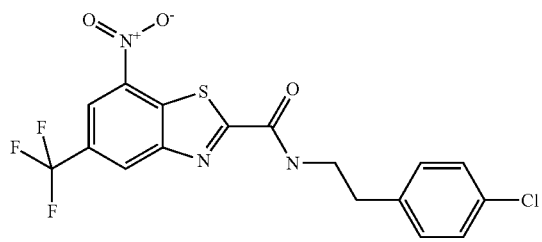 [SMILES: O=C(NCCc1ccc(Cl)cc1)c1nc2cc(C(F)(F)F)cc([N+](=O)[O-])c2s1]

1.1. N-[2-(4-chlorophenyl)ethyl]-7-nitro-5-(trifluoromethyl)-1,3-benzothiazole-2-carboxamide-3-oxide A suspension of 0.3 g (0.89 mmol) of ethyl 7-nitro-5-(trifluoromethyl)-1,3-benzothiazole-2-carboxylate-3-oxide (the synthesis of which is described in Wagner et al., Chem. Ber., 1973, 106, 640-654 compound 4e and Bayer patent DE 2013434, example 7), in 9 ml of methanol is heated with stirring until solubilization, and then cooled to 25° C. 0.157 g (1.01 mmol) of 2-(4-chlorophenyl)ethanamine is added slowly to the solution obtained. The homogeneous reaction mixture is stirred at AT overnight. It is then concentrated under reduced pressure and the residue obtained is purified by silica column chromatography (solvent: cyclohexane/dichloromethane from 60/40 to 0/100). 0.240 g of expected compound is obtained.

LCMS: $(M^+H)^+$=446; tr=9.10 min (Method C).

1.2. N-[2-(4-chlorophenyl)ethyl]-7-nitro-5-(trifluoromethyl)-1,3-benzothiazole-2-carboxamide A suspension of 0.5 g (1.12 mmol) of compound obtained in the previous step, in 7 ml of ethanol, is added dropwise to 0.22 ml (1.26 mmol) of triethyl phosphite.

The reaction mixture is then stirred at 70° C. for 2 hours and then cooled to AT. The precipitate obtained is rinsed with petroleum ether. After drying at 55° C. under reduced pressure, 0.407 g of expected compound is obtained.

Melting point: 140° C. (M); LCMS: $(M^+H)^+$=430; tr=10.16 minutes (Method C).

PREPARATION OF COMPOUNDS NO. 2 TO 13 (ROUTE A)

Example 2—Compound No. 2

7-nitro-N-[2-(tetrahydro-2H-pyran-4-yl)ethyl]-5-(trifluoromethyl)-1,3-benzothiazole-2-carboxamide

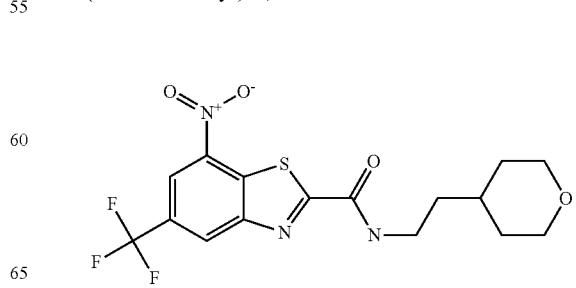

2.1. Ethyl 7-nitro-5-(trifluoromethyl)-1,3-benzo-thiazole-2-carboxylate

A suspension of 20 g (59.48 mmol) of ethyl 7-nitro-5-(trifluoromethyl)-1,3-benzothiazole-2-carboxylate-3-oxide, the synthesis of which is carried out according to a process already described in the literature (K. Wagner et al.; *Chem. Ber.* 106, 640-654, 1973), in 300 ml of ethanol is stirred at AT. After the addition, dropwise, of 11.22 ml (65.43 mmol) of triethyl phosphite, the reaction mixture is stirred at 70° C. for 2 hours, during which time it becomes homogeneous and yellow. Silica is then added thereto and the solvent is evaporated off under reduced pressure. The powder obtained is loaded onto a silica column. The purification is carried out using a cyclohexane/ethyl acetate mixture. The fractions of pure product are evaporated and the residue is taken up with petroleum ether, filtered, and then rinsed with a minimum amount of ethyl ether. After drying at 40° C., under reduced pressure, 16.98 g of expected compound are obtained.

$^1$H NMR (DMSO-d6, 400 MHz) δ ppm: 1.42 (t, 3H); 4.51 (d, 2H); 8.83 (s, 1H); 9.23 (s, 1H); MS: $(M^+H)^+$=321.

2.2. 7-nitro-N-[2-(tetrahydro-2H-pyran-4-yl)ethyl]-5-(trifluoromethyl)-1,3-benzothiazole-2-carboxamide 0.081 g (0.62 mmol) of 2-(tetrahydro-2H-pyran-4-yl)ethanamine is added to a solution of 0.1 g (0.31 mmol) of the compound obtained in the previous step, in 3.1 ml of methanol. The reaction mixture is stirred at AT for 18 hours. The solvent is then evaporated off under reduced pressure and the residue obtained is purified by chromatography under silica (eluent: dichloromethane/methanol from 100/0 to 90/10). 0.081 g of expected compound is obtained.

Melting point: 154° C. (K); LCMS: $(M^+H)^+$=404; tr=8.77 minutes (Method C).

PREPARATION OF COMPOUNDS NO. 14 TO 40 (ROUTE A—AUTOMATED PARALLEL SYNTHESIS)

Example 3—Compound No. 16

N-[2-(3-chlorophenyl)-ethyl]-7-nitro-5-(trifluoromethyl)-1,3-benzothiazole-2-carboxamide In a glass tube, 0.94 g (0.6 mmol) of 2-(3-chlorophenyl) ethanamine is placed in solution in 4 ml of methanol. 0.16 g (0.5 mmol) of the compound of preparation 2.1 in solution in 1 ml of DMF is then added to the mixture. The reaction mixture is stirred at ambient temperature overnight. The methanol is evaporated off and the residue volume is adjusted to 4 ml with DMF. The solution obtained is purified by reverse-phase preparative HPLC according to the following conditions:
  Column: "Xbridge Prep Phenyl 5 μm OBD, Waters, 50 mm×50 mm
  Eluent: water with 0.1% TFA/methanol from 75/25 to 2/98
  Flow rate: 120 ml/min
  The expected product is obtained in trifluoroacetate form.
  LCMS: $(M^+H)^-$=428; tr=1.29 minutes (Method B).

Table I which follows illustrates the chemical structures and the physical properties of some examples of compounds according to the invention.

The column "Salt/Ion/tr (min)/Conditions/Melting point" groups together information relating to the state of the compounds (salt or base), their LCMS characteristics and their melting point when the latter was measured. The first line ("Salt") of each case represents the state of the compound: "/" for a compound in free base form and "TFA" for a compound in trifluoroacetic acid salt form. The second and third lines of each case indicate the LCMS characteristics with, between parentheses, the methods A, B or C used as described previously. The fourth line indicates the melting point with, between parentheses, the letter symbolizing the measuring instrument: K for Kofler bench and M for Mettler-Toledo FP62 instrument.

TABLE I (I)

| Compound No. | X | R | Salt Ion tr (min) (Conditions) Melting point |
|---|---|---|---|
| 1 | —(CH$_2$)$_2$ | 4-Cl-phenyl | / $(M^+H)^+$ = 430 10.16 (C) 140° C. (M) |
| 2 | —(CH$_2$)$_2$ | tetrahydropyran-4-yl | / $(M^+H)^+$ = 404 8.77 (C) 154° C. (K) |
| 3 | —(CH$_2$)$_2$ | pyridin-2-yl | / $(M^+H)^+$ = 397 6.3 (C) 146° C. (K) |
| 4 | —(CH$_2$)$_2$ | C(F)$_3$ | / $(M^+H)^+$ = 388 9.22 (C) 110° C. (K) |
| 5 | —(CH$_2$) | 2-methylpyridin-... | / $(M^+H)^+$ = 383 7.58 (C) 151° C. (K) |
| 6 | —(CH$_2$)$_3$ | morpholin-4-yl | / $(M^+H)^+$ = 419 5.67 (C) 91° C. (K) |
| 7 | —(CH$_2$)$_2$ | 4-methoxyphenyl | / $(M^+H)^+$ = 426 9.69 (C) 180° C. (K) |
| 8 | —(CH$_2$) | cyclohexyl | / $(M^+H)^+$ = 388 10.45 (C) 148° C. (K) |

TABLE I-continued

Structure (I): 7-nitro-5-(trifluoromethyl)benzothiazole-2-carboxamide with NH—X—R substituent.

| Compound No. | X | R | Salt Ion tr (min) (Conditions) Melting point |
|---|---|---|---|
| 9 | —(CH$_2$)$_2$ | 1,2,3,4-tetrahydroisoquinolin-2-yl | / (M$^+$H)$^+$ = 451 8.19 (C) 144° C. (K) |
| 10 | —(CH$_2$) | thiophen-2-yl | / (M$^+$H)$^+$ = 388 9.36 (C) 116° C. (K) |
| 11 | —(CH$_2$) | quinolin-3-yl | / (M$^+$H)$^+$ = 433 7.09 (C) 180° C. (K) |
| 12 | —(CH$_2$)$_2$ | pyrrolidin-1-yl | / (M$^+$H)$^+$ = 389 5.69 (C) 87° C. (K) |
| 13 | —(CH$_2$)$_2$ | 4-(trifluoromethoxy)phenyl | / (M$^+$H)$^+$ = 480 10.47 (C) 150° C. (K) |
| 14 | —(CH$_2$)$_2$ | 4-fluorophenyl | TFA (M$^-$H)$^-$ = 412 1.26 (B) — |
| 15 | —(CH$_2$)$_2$ | 3,4-dimethoxyphenyl | TFA (M$^-$H)$^-$ = 454 1.22 (B) |
| 16 | —(CH$_2$)$_2$ | 3-chlorophenyl | TFA (M$^-$H)$^-$ = 428 1.29 (B) — |
| 17 | —(CH$_2$)$_2$ | 2-hydroxyphenyl | TFA (M$^-$H)$^-$ = 410 1.18 (B) |
| 18 | —(CH$_2$)$_2$ | 4-hydroxyphenyl | TFA (M$^-$H)$^-$ = 410 1.17 (B) |
| 19 | —(CH$_2$) | 4-chlorophenyl | TFA (M$^-$H)$^-$ = 414 1.28 (B) |
| 20 | —(CH$_2$) | 3-methylthiophen-2-yl | TFA (M$^-$H)$^-$ = 386 1.23 (B) |
| 21 | —(CH$_2$)$_2$ | pyridin-2-ylamino | TFA (M$^-$H)$^-$ = 412 0.95 (A) |
| 22 | —(CH$_2$)$_2$ | thiomorpholin-4-yl | TFA (M$^+$H)$^+$ = 421 0.93 (A) |
| 23 | —(CH$_2$) | 3-methylpyridin-2-yl | TFA (M$^+$H)$^+$ = 383 1.00 (A) |
| 24 | —(CH$_2$) | 2-(morpholin-4-yl)phenyl | TFA (M$^+$H)$^+$ = 467 1.27 (A) |
| 25 | —(CH$_2$)$_2$ | 2,3-dimethylpyridin-3-yl | TFA (M$^+$H)$^+$ = 411 1.00 (A) |

TABLE I-continued (I) Structure: 7-nitro-5-trifluoromethyl-benzothiazole-2-carboxamide with NH—X—R substituent

| Compound No. | X | R | Salt Ion tr (min) (Conditions) Melting point |
|---|---|---|---|
| 26 | —(CH₂) | 1-phenylethyl-morpholine | TFA (M⁺H)⁺ = 481 1.05 (A) — |
| 27 | —(CH₂)₂ | 4-phenyl-2,2-dimethyl-tetrahydropyran | TFA (M⁺H)⁺ = 508 1.31 (A) — |
| 28 | —(CH₂)₃ | 2,6-dimethylpyridine | TFA (M⁺H)⁺ = 411 0.97 (A) — |
| 29 | —(CH₂)₂ | 3,4-dimethyl-5-methyl-isoxazole | TFA (M⁺H)⁺ = 429 1.20 (A) — |
| 30 | —(CH₂)₂ | pyrazole | TFA (M⁺H)⁺ = 386 1.13 (A) — |
| 31 | —(CH₂)₂ | morpholine | TFA (M⁺H)⁺ = 405 0.90 (A) — |
| 32 | —(CH₂) | 3-methyl-morpholine-benzyl | TFA (M⁺H)⁺ = 481 1.00 (A) — |
| 33 | —(CH₂) | 2,2-dimethyl-morpholinyl | TFA (M⁺H)⁺ = 433 0.94 (A) — |
| 34 | —(CH₂)₃ | 3-methylpyridine | TFA (M⁺H)⁺ = 411 0.98 (A) — |
| 35 | —(CH₂)₂ | thiophene | / (M⁻H)⁻ = 400 1.25 (B) — |
| 36 | —(CH₂)₂ | 2-methyl-4-methyl-5-chloro-thiazole | / (M⁺H)⁺ = 451 1.27 (A) — |
| 37 | —(CH₂)₃ | 4,5-dimethyl-thiazole | / (M⁺H)⁺ = 431 1.17 (A) — |
| 38 | —(CH₂)₂ | benzoxazole | / (M⁺H)⁺ = 437 1.22 (A) — |
| 39 | —(CH₂)₂ | 2-methyl-4-methylmethyl-thiazole | / (M⁺H)⁺ = 431 1.23 (A) — |
| 40 | —(CH₂)₂ | 2,4,5-trimethyl-thiazole | / (M⁺H)⁺ = 431 1.21 (A) — |

The compounds corresponding to general formula (I) which is the subject of the invention were subjected to microbiological tests which showed their value as therapeutically active substances.

MEASUREMENT OF THE INHIBITORY ACTIVITY OF THE COMPOUNDS ACCORDING TO THE INVENTION WITH RESPECT TO *MYCOBACTERIUM TUBERCULOSIS*

The in vitro test used makes it possible to identify molecules with an antimicrobial activity on the *Mycobacterium tuberculosis* $H_{37}R_v$ strain. It is a biological safety level 3 bacterium.

Materials and Methods

The test used is Alamar blue (MABA). It is a colorimetric test which makes it possible to determine the MIC (minimum inhibitory concentration) of antibacterials. Alamar blue is an oxidation-reduction indicator which goes from blue to pink in the event of bacterial growth. Resazurin (blue and not fluorescent) is reduced to resorufin (pink and fluorescent) by live bacteria. The plate is therefore read visually or by measurement of fluorescence. The fluorescence intensity is proportional to the number of live bacteria.

Thus, the closer the fluorimetric MIC value is to zero, the smaller the amount of product required to inhibit total growth of the bacteria.

Compounds 2, 7, 9, 14, 15, 16, 17, 18, 21, 22, 25, 26, 27, 36, 38, 39, and 40 have fluorimetric MICs of less than 0.5 µM with respect to the growth of *Mycobacterium tuberculosis*.

These experiments demonstrate that the compounds according to the present invention have a notable inhibitory activity on *M. tuberculosis* growth. Indeed, the standard antibiotics generally have results in the above test of the order of a micromolar or a tenth of a micromolar. For example, rifampicin inhibits *M. tuberculosis* growth with an MIC of 0.12 μM and isoniazid inhibits *M. tuberculosis* growth with an MIC of 0.36 μM in the same test.

The compounds according to the invention, namely the compounds corresponding to formula (I), also exhibit good microbiological properties and are particularly suitable for use in the preparation of a medicament, in particular of a narrow-spectrum antibiotic for the treatment and/or prevention of tuberculosis.

In particular, these antibiotics exhibit an antimicrobial action against *M. tuberculosis* for the treatment and/or prevention of tuberculosis.

Thus, according to another of its aspects, a subject of the invention is medicaments which comprise a compound of formula (I), or an addition salt thereof with a pharmaceutically acceptable acid or base of the compound of formula (I).

These medicaments are of therapeutic use in particular in the treatment and/or prevention of tuberculosis.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt of said compound, and also at least one pharmaceutically acceptable excipient.

Said excipients are chosen, according to the pharmaceutical form and the mode of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above or salt thereof can be administered in unit administration form, as a mixture with conventional pharmaceutical excipients, to animals and to human beings for the prophylaxis (to be adapted on a case-by-case basis) or the treatment of the above disorders or diseases.

The suitable unit administration forms include oral administration forms, such as tablets, soft or hard capsules, powders, granules and oral solutions or suspensions, sublingual, buccal intratracheal, intraocular and intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit administration form of a compound according to the invention in tablet form can comprise the following constituents:

| | |
|---|---|
| Compound according to the invention | 50.0 mg |
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

There may be particular cases where higher or lower dosages are suitable, such dosages do not depart from the context of the invention. According to the usual practice, the dosage suitable for each patient is determined by the physician according to the mode of administration and the weight and response of said patient.

According to another of its aspects, the present invention also relates to the use of the compounds of formula (I), or a pharmaceutically acceptable salt or hydrate or solvate thereof (to be adapted on a case-by-case basis), for the treatment and/or prevention of bacterial infections caused by mycobacteria such as *M. smegmatis* or *M. phlei*, or by other microorganisms such as *Nocardia brasiliensis, Nocardia absessus* or *Corynebacterium diphtheria*, for example.

Thus, one of the aspects of the invention relates to the use of the compounds of formula (I) or a pharmaceutically acceptable salt or hydrate or solvate thereof (to be adapted on a case-by-case basis), for the treatment and/or prevention of infectious diseases such as tuberculosis, leprosy, nocardiosis, diphtheria, pulmonary mycobacterial infection, cutaneous mycobacterial infection, atypical mycobacterial infection and mycobacteriosis.

The term "tuberculosis" comprises infections caused by bacilli of the tuberculosis complex (*M. tuberculosis, M. bovis* and *M. africanum*) which are all pathogenic to humans. Pulmonary tuberculosis is by far the most common and the most widespread; it is tuberculosis of the lung, of the larynx, of the trachea and of the bronchi, tuberculosis of intrathoracic lymph nodes, respiratory tuberculosis of the pleura, primary respiratory tuberculosis and any other respiratory tuberculosis. Even though they are less common, lymph node tuberculosis and extrapulmonary tuberculosis, nervous system tuberculosis, such as tuberculous meningitis, tuberculous leptomeningitis, brain tuberculomas and any other nervous system tuberculosis, or else bone or joint tuberculosis, tuberculosis of the urogenital system, peripheral tuberculous lymphadenopathy, intestinal, peritoneal and/or mesenteric gland tuberculosis, cutaneous tuberculosis and tuberculosis of the subcutaneous tissues, tuberculosis of the eye, of the ear or of the adrenal glands, and also disseminated tuberculosis also exist. The term "leprosy" (Hansen's disease) comprises infections caused by *Mycobacterium leprae*: indeterminate leprosy, tuberculoid leprosy, borderline leprosy, borderline tuberculoid leprosy, lepromatous leprosy, and also the other forms of leprosy.

The term "diphtheria" comprises pharyngeal diphtheria, nasopharyngeal diphtheria, cutaneous diphtheria and also the other forms of diphtheria.

The term "nocardiosis" comprises pulmonary nocardiosis, cutaneous nocardiosis and the other forms of nocardiosis.

According to another of its aspects, the present invention also relates to a method for treating the pathological conditions indicated above, which comprises the administration, to a patient, of an effective dose of a compound of formula (I).

The invention claimed is:
1. A compound corresponding to formula (I):

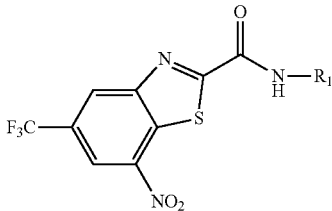

for which, R₁ represents:
  a (C₁-C₄)alkyl substituted with:
  one or more halogen atoms;
  an aryl substituted with one or more groups chosen, independently of one another, from an OH, (C₁-C₃)alkoxy, (C₃-C₆)heterocycloalkyl or (C₁-C₃)fluoroalkoxy group;
  a heteroaryl optionally substituted with one or more groups chosen, independently of one another, from a (C₁-C₄) alkyl group and a halogen atom;
  an unsubstituted heteroaryl-NH;
  an unsubstituted (C₃-C₆)cycloalkyl;
  a (C₃-C₆)heterocycloalkyl optionally substituted with one or more groups chosen, independently of one another, from a (C₁-C₃)alkyl, aryl and aryl (C₁-C₃)alkyl group; or
  a (C₁-C₄)alkyl disubstituted with:
  an unsubstituted aryl; and
  an unsubstituted (C₃-C₆)heterocycloalkyl;
  in the form of a base or an addition salt with an acid or with a base.

2. The compound of formula (I) as claimed in claim 1, characterized in that R¹ represents:
  a (C₁-C₄)alkyl radical substituted with:
  one or more fluorine atoms;
  a phenyl substituted with one or more groups chosen, independently of one another, from an OH, methoxy, morpholine or trifluoromethoxy group;
  a pyridinyl, isoxazolyl, pyrazolyl, thienyl, benzoxazolyl, tetrahydroisoquinolinyl, quinolinyl and thiazolyl group optionally substituted with one or more groups chosen, independently of one another, from a methyl or ethyl group or a chlorine atom;
  an unsubstituted pyridinyl-NH group;
  an unsubstituted cyclohexyl group;
  a tetrahydropyranyl group, a morpholinyl group, a pyrrolidinyl group and a thiomorpholinyl group optionally substituted with one or more groups chosen, independently of one another, from a methyl, phenyl and benzyl group; or
  a (C₁-C₄)alkyl radical disubstituted with:
  an unsubstituted phenyl; and
  an unsubstituted morpholinyl group;
  in the form of a base or of an addition salt with an acid or with a base.

3. A compound selected from a group consisting of:
N-[2-(4-chlorophenypethyl]-7-nitro-5-(trifluoromethyl)-1,3-benzothiazole-2-carboxamide;
7-nitro-N-[2-(tetrahydro-2H-pyran-4-yl)ethyl]-5-(trifluoromethyl)-1,3-benzothiazole-2-carboxamide;
7-nitro-N-(2-pyridin-2-ylethyl)-5-(trifluoromethyl)-1,3-benzothiazole-2-carboxamide;
7-nitro-5-(trifluoromethyl)-N-(3,3,3-trifluoropropyl)-2-benzothiazolecarboxamide;
7-nitro-N-(pyridin-2-ylmethyl)-5-(trifluoromethyl)-1,3-benzothiazole-2-carboxamide;
N-[3-(4-morpholinyl)propyl]-7-nitro-5-(trifluoromethyl)-2-benzothiazolecarboxamide;
N-[2-(4-methoxyphenypethyl]-7-nitro-5-(trifluoromethyl)-1,3benzothiazole-2-carboxamide;
N-(cyclohexylmethyl)-7-nitro-5-(trifluoromethyl)-1,3-benzothiazole-2-carboxamide;
N-[2-(1,2,3,4-tetrahydroisoquinolin-2(1H)-yl)ethyl]-7-nitro-5-(trifluoromethyl)-1,3-benzothiazole-2-carboxamide;
7-nitro-N-(thien-2-ylmethyl)-5-(trifluoromethyl)-1,3-benzothiazole-2-carboxamide;
7-nitro-N-(quinolin-3 -ylmethyl)-5-(trifluoromethyl)-1,3-benzothiazole-2-carboxamide;
7-nitro-N-(2-pyrrolidin-1-ylethyl)-5-(trifluoromethyl)-1,3-benzothiazole-2-carboxamide;
7-nitro-N-{2-[4-trifluoromethoxy)phenyl]ethyl}-5-(trifluoromethyl)-1,3 -benzothiazole-2-carboxamide;
N-[2-(4-fluorophenypethyl]-7-nitro-5-(trifluoromethyl)-1,3-benzothiazole-2-carboxamide;
N-[2-(3,4-dimethoxypheny)ethyl]-7-nitro-5-(trifluoromethyl)-1,3-benzothiazole-2-carboxamide;
N-[2-(3 -chlorophenypethyl]-7-nitro-5-(trifluoromethyl)-1,3-benzothiazole-2-carboxamide;
N-[2-(2-hydroxyphenyl)ethyl]-7-nitro-5-(trifluoromethyl)-1,3-benzothiazole-2-carboxamide;
N-[2-(4-hydroxyphenyl)ethyl]-7-nitro-5 -(trifluoromethyl)-1,3-benzothiazole-2-carboxamide;
N-(4-chlorobenzyl)-7-nitro-5-(trifluoromethyl)-1,3-benzothiazole-2-carboxamide;
7-nitro-N-(thien-3-ylmethyl)-5-(trifluoromethyl)-1,3-benzothiazole-2-carboxamide;
7-nitro-N-[2-(pyridin-2-ylamino)ethyl]-5-(trifluoromethyl)-1,3-benzothiazole-2-carboxamide;
7-nitro-N-[2-thiomorpholin-4-ylethyl]-5-(trifluoromethyl)-1,3-benzothiazole-2-carboxamide;
7-nitro-N-(pyridin-3-ylmethyl)-5-(trifluoromethyl)-1,3-benzothiazole-2-carboxamide;
N-(2-morpholin-4-ylbenzyl)-7-nitro-5-(trifluoromethyl)-1,3-benzothiazole-2-carboxamide;
N-[2-(3-methylpyridin-2-yl)ethyl]-7-nitro-5-(trifluoromethyl)-1,3-benzothiazole-2-carboxamide;
N-(2-morpholin-4-yl-2-phenylethyl)-7-nitro-5-(trifluoromethyl)-1,3-benzothiazole-2-carboxamide;
N-[2-(2,2-dimethyl-4-phenyltetrahydro-2H-pyran-4-yl) ethyl]-7-nitro-5-(trifluoromethyl)-1,3-benzothiazole-2-carboxamide;
N-[2-(6-methylpyridin-2-yl)ethyl]-7-nitro-5-(trifluoromethyl)-1,3-benzothiazole-2-carboxamide;
N-[3-(3,5-dimethylisoxazol-4-yl)propyl]-7-nitro-5-(trifluoromethyl)-1,3-benzothiazole-2-carboxamide;
7-nitro-N-[2-(1H-pyrazol-1-yl)ethyl]-5-(trifluoromethyl)-1,3-benzothiazole-2-carboxamide;
N-(2-morpholin-4-ylethyl)-7-nitro-5-(trifluoromethyl)-1,3-benzothiazole-2-carboxamide;
N-[(4-benzylmorpholin-2-yl)methyl]-7-nitro-5-(trifluoromethyl)-1,3-benzothiazole-2-carboxamide;
N-(2-methyl-2-morpholin-4-ylpropyl)-7-nitro-5-(trifluoromethyl)-1,3-benzothiazole-2-carboxamide;
7-nitro-N-(3-pyridin-3-ylpropyl)-5-(trifluoromethyl)-1,3-benzothiazole-2-carboxamide;
7-nitro-N-(2-thien-2-ylethyl)-5-(trifluoromethyl)-1,3-benzothiazole-2-carboxamide;

N-[2-(5-chloro-4-methyl-1,3-thiazol-2-yl)ethyl]-7-nitro-5-(trifluoromethyl)-1,3-benzothiazole-2-carboxamide;
N-[3-(4-methyl-1,3-thiazol-5-yl)propyl]-7-nitro-5-(trifluoromethyl)-1,3-benzothiazole-2-carboxamide;
N-[2-(1,3-benzoxazol-2-yl)ethyl]-7-nitro-5-(trifluoromethyl)-1,3-benzothiazole-2-carboxamide;
N-[2-(4-ethyl-1,3-thiazol-2-yl)ethyl]-7-nitro-5-(trifluoromethyl)-1,3-benzothiazole-2-carboxamide and
N-[2-(4,5-dimethyl-1,3-thiazol-2-yl)ethyl]-7-nitro-5-(trifluoromethyl)-1,3-benzothiazole-2-carboxamide.

4. A process for preparing a compound corresponding to formula (I):

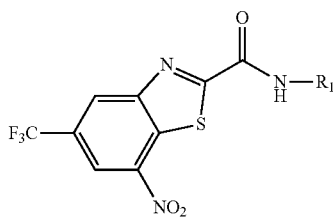

for which, $R_1$ represents:
a $(C_1-C_4)$alkyl substituted with:
one or more halogen atoms;
an aryl optionally substituted with one or more groups chosen, independently of one another, from an OH, $(C_1-C_3)$alkoxy, $(C_3-C_6)$heterocycloalkyl 1 or $C_1-C_3)$fluoroalkoxy group and a halogen atom;
a heteroaryl optionally substituted with one or more groups chosen, independently of one another, from a $(C_1-C_4)$ alkyl group and a halogen atom;
an unsubstituted heteroaryl-NH;
an unsubstituted $(C_3-C_6)$cycloalkyl;
a $(C_3-C_6$ heterocycloalkyl optionally substituted with one or more groups chosen, independently of one another, from a $(C_1-C_3)$alkyl, aryl and aryl$(C_1-C_3)$alkyl group; or
a $(C_1-C_4)$alkyl disubstituted with:
an unsubstituted aryl; and
an unsubstituted $(C_3-C_6)$heterocycloalkyl;
in the form of a base or an addition salt with an acid or with a base, comprising reacting a compound of formula (II):

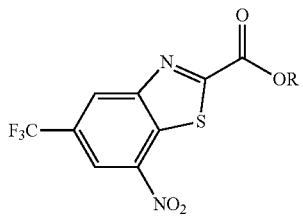

wherein R represents a $(C_1-C_4)$alkyl, with an amine of formula (III):

wherein $R_1$ is as defined for the compounds of formula (I).

5. A pharmaceutical composition comprising a compound corresponding to formula (I):

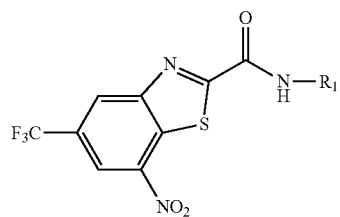

for which, $R_1$ represents:
a $(C_1-C_4)$alkyl substituted with:
one or more halogen atoms;
an aryl optionally substituted with one or more groups chosen, independently of one another, from an OH, $(C_1-C_3)$alkoxy, $(C_3-C_6)$heterocycloalkyl or $(C_1-C_3)$fluoroalkoxy group and a halogen atom;
a heteroaryl optionally substituted with one or more groups chosen, independently of one another, from a $(C_1-C_4)$ alkyl group and a halogen atom;
an unsubstituted heteroaryl-NH;
an unsubstituted $(C_3-C_6)$cycloalkyl;
a $(C_3-C_6)$heterocycloalkyl optionally substituted with one or more groups chosen, independently of one another, from a $(C_1-C_3)$alkyl, aryl and aryl $(C_1-C_3)$alkyl group; or
a $(C_1-C_4)$alkyl disubstituted with:
an unsubstituted aryl; and
an unsubstituted $(C_3-C_6)$heterocycloalkyl;
in the form of a base or of an addition salt with an acid or with a base.

6. The pharmaceutical composition of claim 5, further comprising at least one pharmaceutically acceptable excipient.

7. A method for treating tuberculosis in a patient in need thereof comprising administering to said patient a therapeutically effective amount of a narrow-spectrum antibiotic medicament comprising a compound corresponding to formula (I):

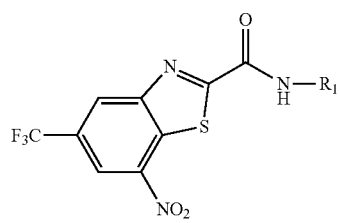

for which, $R_1$ represents:
a $(C_1-C_4)$alkyl substituted with:
one or more halogen atoms;
an aryl optionally substituted with one or more groups chosen, independently of one another, from an OH, $(C_1-C_3)$alkoxy, $(C_3-C_6)$heterocycloalkyl or $(C_1-C_3)$fluoroalkoxy group and a halogen atom;
a heteroaryl optionally substituted with one or more groups chosen, independently of one another, from a $(C_1-C_4)$ alkyl group and a halogen atom;
an unsubstituted heteroaryl-NH;
an unsubstituted $(C_3-C_6)$cycloalkyl;
a $(C_3-C_6$ heterocycloalkyl optionally substituted with one or more groups chosen, independently of one another, from a $(C_1-C_3)$alkyl, aryl and aryl $(C_1-C_3)$alkyl group; or a ($C_1$-$C_4$)alkyl disubstituted with:
an unsubstituted aryl; and
an unsubstituted ($C_3$-$C_6$)heterocycloalkyl;
in the form of a base or an addition salt with an acid or with a base.

8. The method of claim 7, characterized in that the antibiotic has an antimicrobial action for the treatment and/or prevention of *tuberculosis*.

9. The method of claim 8, characterized in that the antibiotic has an antimicrobial action against *M. tuberculosis*.

10. A pharmaceutical composition comprising a compound according to claim 3.

11. The pharmaceutical composition of claim 10, further comprising at least one pharmaceutically acceptable excipient.

12. A method for treating tuberculosis in a patient in need thereof comprising administering to said patient a therapeutically effective amount of a narrow-spectrum antibiotic medicament comprising a compound according to claim 3.

13. The method of claim 12, characterized in that the antibiotic has an antimicrobial action for the treatment and/or prevention of *tuberculosis*.

14. The method of claim 13, characterized in that the antibiotic has an antimicrobial action against *M tuberculosis*.

* * * * *

UNITED STATES PATENT AND TRADEMARK OFFICE
CERTIFICATE OF CORRECTION

| | |
|---|---|
| PATENT NO. | : 8,993,561 B2 |
| APPLICATION NO. | : 13/988868 |
| DATED | : March 31, 2015 |
| INVENTOR(S) | : Alain Pellet |

It is certified that error appears in the above-identified patent and that said Letters Patent is hereby corrected as shown below:

In the Claims:

Column 31, claim number 2, line number 37, please replace "characterized in that $R^1$ represents" with --characterized in that $R_1$ represents--;

Column 31, claim number 3, line number 61, please replace "selected from a group consisting of" with --selected from the group consisting of--;

Column 31, claim number 3, line number 62, please replace "(4-chlorophenypethyl]" with --(4-chlorophenyl)ethyl]--;

Column 32, claim number 3, line number 7, please replace "(4-methoxyphenypethyl]" with --(4-methoxyphenyl)ethyl]--;

Column 32, claim number 3, line number 16, please replace "(quinolin-3 –ylmethyl)" with --(quinolin-3–ylmethyl)--;

Column 32, claim number 3, line number 22, please replace "1,3 –benzothiazole-2-" with --1,3–benzothiazole-2- --;

Column 32, claim number 3, line number 23, please replace "(4-fluorophenypethyl]" with --(4-fluorophenyl)ethyl]--;

Signed and Sealed this
Eleventh Day of August, 2015

Michelle K. Lee
*Director of the United States Patent and Trademark Office*

Column 32, claim number 3, line number 25, please replace "(3,4-dimethoxypheny )ethyl" with --(3,4-dimethoxyphenyl)ethyl--;

Column 32, claim number 3, line number 27, please replace "(3 -chlorophenypethyl]" with --(3-chlorophenyl)ethyl]--;

Column 32, claim number 3, line number 31, please replace "7-nitro-5  -(trifluorom-" with --7-nitro-5-(trifluorom- --;

Column 33, claim number 4, line numbers 32-33, please replace "($C_3$-$C_6$)heterocycloalkyl 1 or $C_1$-$C_3$)fluoroalkoxy" with --($C_3$-$C_6$)heterocycloalkyl or ($C_1$-$C_3$)fluoroalkoxy--;

Column 33, claim number 4, line number 39, please replace "a ($C_3$-$C_6$ heterocycloalkyl optionally" with --a ($C_3$-$C_6$)heterocycloalkyl optionally--;

Column 34, claim number 7, line number 64, please replace "a ($C_3$-$C_6$ heterocycloalkyl optionally" with --a ($C_3$-$C_6$)heterocycloalkyl optionally--;

Column 35, claim number 8, line numbers 7-8, please replace "prevention of *tuberculosis*" with --prevention of tuberculosis--;

Column 35, claim number 13, line number 22, please replace "prevention of *tuberculosis*" with --prevention of tuberculosis--;

Column 35, claim number 14, line number 24, please replace "action against *M tuberculosis.*" with --action against *M. tuberculosis.*--.